United States Patent [19]
Vince et al.

[11] Patent Number: 5,567,703
[45] Date of Patent: Oct. 22, 1996

[54] METHOD FOR TREATING HIV INFECTIONS WITH DIDEOXYCARBOCYCLIC NUCLEOSIDES

[75] Inventors: Robert Vince, St. Paul, Minn.; Mei Hua, Beijing, China

[73] Assignee: Regents of the University of Minnesota, Minneapolis, Minn.

[21] Appl. No.: 441,072

[22] Filed: May 15, 1995

Related U.S. Application Data

[60] Division of Ser. No. 290,185, Aug. 15, 1994, which is a continuation-in-part of Ser. No. 495,341, Mar. 19, 1990, abandoned, which is a division of Ser. No. 278,652, Dec. 5, 1988, Pat. No. 4,931,559, which is a continuation-in-part of Ser. No. 146,252, Jan. 20, 1988, Pat. No. 4,916,224.

[51] Int. Cl.⁶ .................................................. A61K 31/52
[52] U.S. Cl. ......................... 514/261; 514/262; 514/75
[58] Field of Search ................................ 514/75, 261, 262

[56] References Cited

U.S. PATENT DOCUMENTS 4,968,674  11/1990  Taniyama et al. ............................ 514/63

Primary Examiner—Russell Travers
Attorney, Agent, or Firm—Schwegman, Lundberg, Woessner & Kluth, P.A.

[57] ABSTRACT

A therapeutic method is provided, employing an antiviral compound of the general formula:

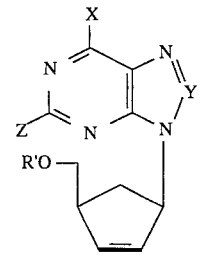

wherein Z is H, OR' or $N(R)_2$, wherein R' is H, $(C_1-C_4)$alkyl, aryl, CHO, $(C_1-C_{16})$alkanoyl or $O{=}P(OH)_2$, Y is CH or N, and X is selected from the group consisting of H, $N(R)_2$, SR, OR' or halogen, wherein R is H, lower$(C_1-C_4)$alkyl, aryl or mixtures thereof, and the pharmaceutically acceptable salts thereof.

22 Claims, 2 Drawing Sheets

METHOD FOR TREATING HIV INFECTIONS WITH DIDEOXYCARBOCYCLIC NUCLEOSIDES

GRANT INFORMATION

This invention was made with Government support under Grant No. 5 R 01 CA23263, awarded by the National Institutes of Health. The Government has certain rights in this invention.

CROSS-REFERENCE TO RELATED APPLICATION

This is a division, of application Ser. No. 08/290,185, filed Aug. 15, 1994, which is a continuation-in-part of U.S. patent application Ser. No. 07/495,341, now abandoned, filed Mar. 19, 1990, which is a divisional of U.S. patent application Ser. No. 278,652 (filed Dec. 5, 1988) (now U.S. Pat. No. 4,931,559) which is a continuation-in-part of U.S. patent application Ser. No. 146,252, filed Jan. 20, 1988 (now U.S. Pat. No. 4,916,224).

FIELD OF THE INVENTION

The present invention relates to a therapeutic method employing dideoxycarbocyclic nucleosides which exhibit antiviral activity.

BACKGROUND OF THE INVENTION

Despite intensive effort to discover drugs that may be of value in the systemic treatment of human immunodeficiency virus (HIV) infections, such infections have been singularly resistant to chemotherapy. The intracellular and intimate relation to nuclear metabolism of virus reproduction makes it difficult to destroy a virus without irreparable damage to the host cell.

The discovery of the antiviral activity of vidarabine (9-β-D-arabinofuranosyladenine monohydrate) has led to the preparation of a large number of synthetic nucleosides. To date, only one synthetic nucleoside, 3'-azido-3'-deoxythymidine has been approved for treating certain AIDS patients, but it is a palliative, not a cure.

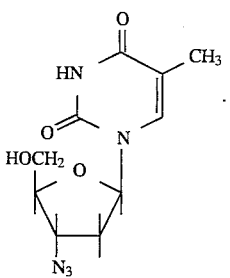

(AZT)

Although AZT is specifically active against retroviruses, its use has led to side effects, including anemia, headache, confusion, anxiety, nausea and insomnia. The nucleoside analog, 2',3'-dideoxycytidine (DDC), exhibits an in vitro $TI_{50}$ of ca. 300 against HIV and may exhibit fewer side effects than AZT, but may also be eliminated more rapidly from the body.

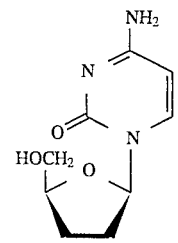

(DDC)

The synthesis of adenine ("6-amino-purine") nucleoside analogs in which the pentose sugar has been replaced with tris(hydroxy)-substituted cyclopentyl residues has yielded compounds with substantial cytotoxic and antiviral activity. For example, the carbocyclic analog of vidarabine, cyclaridine, is highly active against HSV-2, but exhibits a low therapeutic index ($TI_{50}=10$) against HIV in vitro. Likewise, the carbocyclic analog of AZT is inactive against HIV. Therefore, it is clear that the structure-activity relationships between the variously substituted carbocyclic nucleosides which have been prepared and tested remain ill-defined.

Thus, a substantial need exists for chemotherapeutic agents effective to protect mammalian cells against infection by viruses such as HSV-2, HIV, varicella-zoster, vaccinia, human cytomegalovirus (HCMV) and the like.

SUMMARY OF THE INVENTION

The present invention is directed to hydroxy-methylcyclopentenyl-substituted purines and 8-aza-purines of the formula (I):

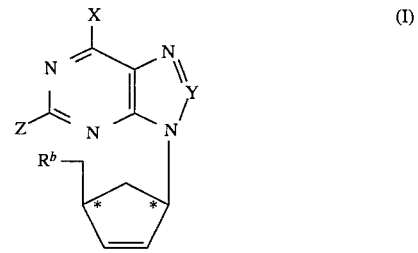

wherein Z is H, OR' or $N(R)_2$, Y is CH or N, and X is selected from the group consisting of H, $N(R)_2$, SR, OR' and halogen, wherein R is H, lower($C_1$–$C_4$)alkyl, aryl or mixtures thereof, wherein R' is H, ($C_1$–$C_4$)alkyl, aryl, CHO, ($C_1$–$C_{16}$)alkanoyl, or O=P(OH)$_2$, and the pharmaceutically acceptable salts thereof. Preferably, X is Cl, OR', most preferably OH; or $N(R)_2$, Y is CH, R is phenyl or H, and R' is H or acetyl. As used herein, the term "aryl" includes substituted and unsubstituted aralkyl (preferably ar($C_1$–$C_4$)alkyl) moieties. Preferred aryl moieties include phenyl, tolyl, xylyl, anisyl, or phen($C_1$–$C_4$)alkyl, e.g., benzyl or phenethyl. Certain of these compounds are effective antiviral and/or cytotoxic agents or are intermediates useful for the preparation thereof.

A given compound within the scope of the formula has two optically active centers, indicated by the symbol (*) in formula I, either of which can exhibit R, S or RS stereochemistry. Therefore, single resolved, optically active enantiomers and diasteriomers of the present compounds are preferred embodiments of the present invention, although partially resolved and racemic (±) mixtures are also within the scope of the invention. The four stereoisomers of the compound of formula I are depicted below:

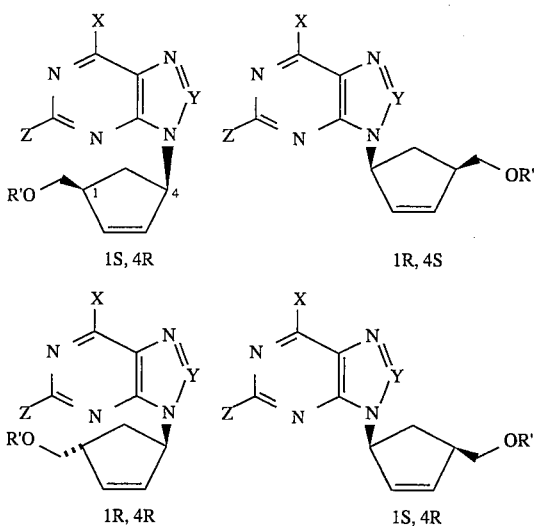

wherein X, Y, Z and R' are defined hereinabove. The stereoconfigurations are given using the cyclopent-2-en-4-yl-1-carbinol nomenclature.

Certain of the compounds of formula I may exist as a mixture of tautomeric forms and all such tautomers are included within the scope of the invention.

A preferred compound of the invention is the optically active enantiomer of the formula II:

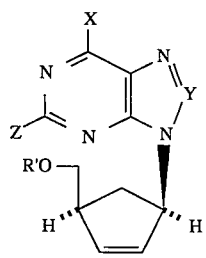
(II)

wherein X, Y, Z and R' are as defined above and the stereochemistry at the optically active centers is as depicted. A wedged line indicates a bond extending above the plane of the cyclopentenyl ring, while a dashed line indicates a bond extending below the plane of the cyclopentenyl ring.

Although generally compounds of formula I are not active against HSV-1, it is expected that some of them will exhibit specific antiviral activity against other viruses such as hepatitis, HSV-2, EBV, RSV, PRV, HCMV and/or HIV, as well as against other retroviruses, such as those believed to cause T-cell leukemia. Specifically, the racemic compound of formula I, wherein X is OH, Z is $NH_2$, Y is CH and R' is H (14a), strongly inhibits HIV infectivity in vitro. The $TI_{50}$ of this compound varied with the infected cell line which was used to assay for anti-HIV activity, but generally fell between 200–400, and was determined to be as high as 667 in one assay. The acetate ester (R'=Ac) of 14a was also active against HIV, giving 28% inhibition at 6 μg/ml. Compound 14a is also active against HSV-1.

The fully resolved compound of formula II, wherein X is OH, Z is $NH_2$, Y is CH and R' is H ((−)14a) is also highly active against HIV [(1'R,4'S)-2-amino-1,9-dihydro-9-[4'-hydroxymethyl-2'-cyclopenten-1-yl]-6H-purin-6-one, or (1S, 4R)-4-(2-amino-6-hydroxy-9H-purin-9-yl)-2-cyclopentenylcarbinol]. Compounds of formula I wherein X is Cl or $N(R)_2$, Y is CH, Z is $NH_2$ and R' is H (13a and 15a, respectively) are also active against HIV, as are compounds wherein X is Cl, $NH_2$ or SH, Y is CH, Z is H and R' is H (7a, 9a and 10a, respectively). Compounds 7a, 9a and 10a, as well as compounds of the formula I wherein Y=N, Z=$NH_2$, X=Cl, $NH_2$ or OH and R' is H (16a, 18a and 17a), are cytotoxic to cultured P-388 leukemia cells. It is believed that the antiviral activity is due to an inhibitory effect on the ability of viruses to infect normal mammalian cells. The present invention is also directed to the intermediate compound of the formula (III):

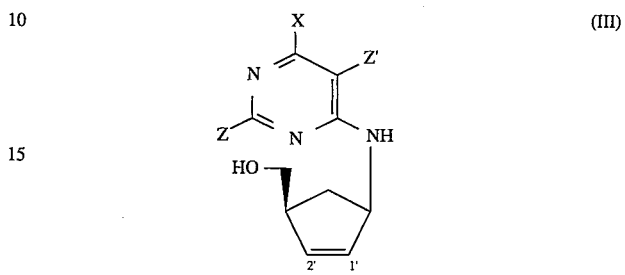
(III)

wherein Z is H or $NH_2$, Z' is H or $NH_2$, and X is halogen, preferably Cl, which is useful for the preparation of the purines of the invention. Preferably, Z is $NH_2$, and Z' is H or both Z and Z' are $NH_2$. However, the compounds where X=Cl, Z=$NH_2$ and Z'=H or $NH_2$ are not active against HIV.

The (3-hydroxymethylcyclopentenyl)pyrimidine analog, 20a, is also within the scope of the present invention. Its synthesis from cyclopentene 2a is outlined in Scheme I, below.

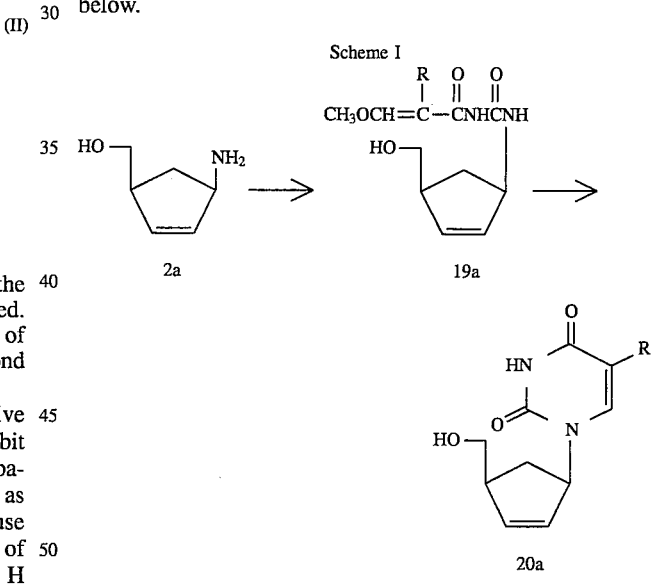

In compounds 19a and 20a, R can be $CH_3$ or H. Thus, it is expected that certain of the compounds of the present invention will be useful against viral infections or virus-associated tumors, and the method of their use to inhibit viral infectivity or tumor growth in vitro or in vivo is also within the scope of the present invention..

DETAILED DESCRIPTION OF THE INVENTION

Figure 1:
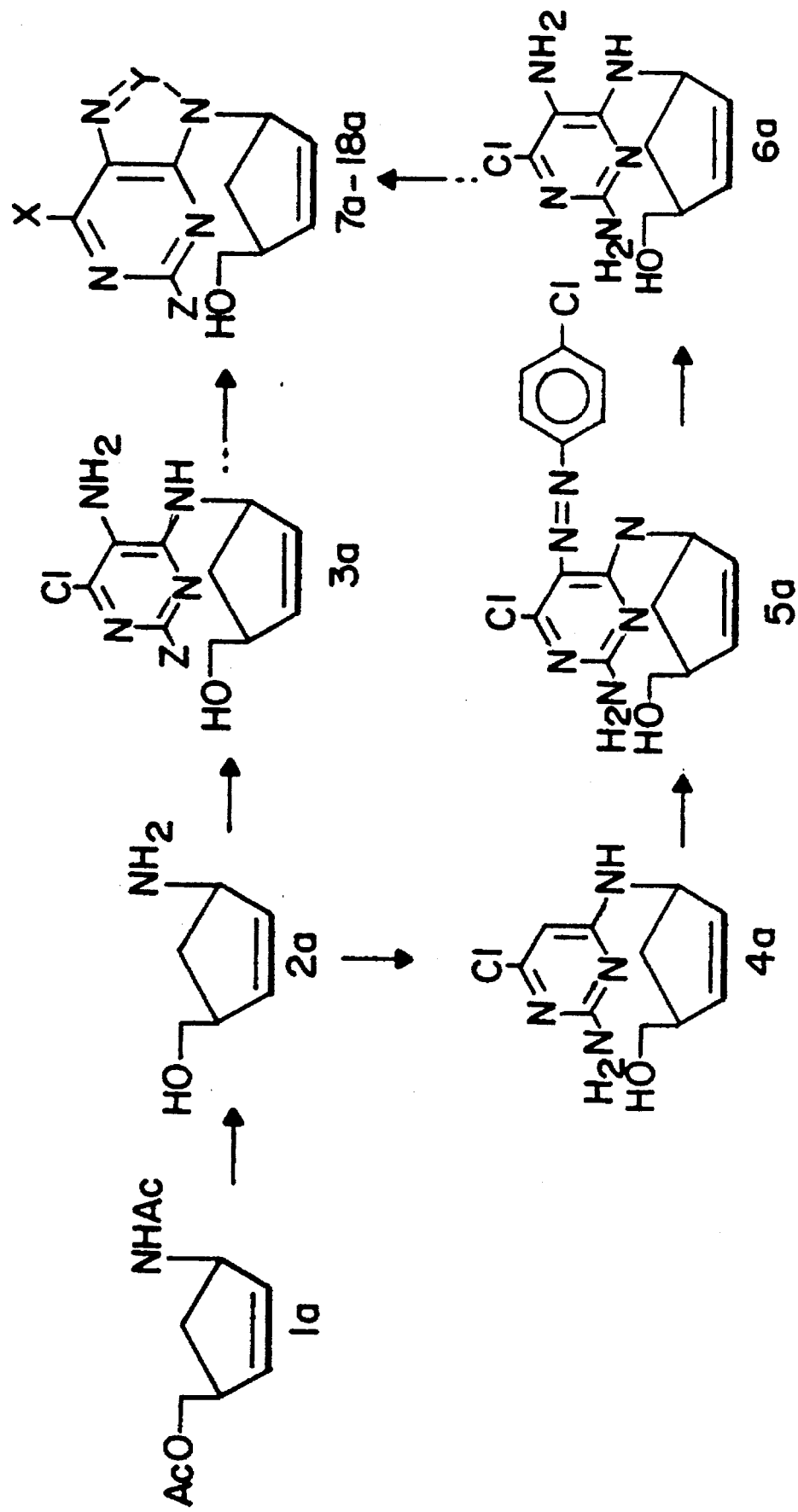
FIG. 1 is a flow diagram summarizing the synthesis of the purines of the present invention.

FIG. 1 outlines the synthesis of preferred compounds of the invention from starting material 1a. The structural formulas and some of the properties of compounds 7a–18a are summarized on Table I, below.

TABLE I

| Compound No. | X | Y | M.P. (°C.) | Rf | Yield (%) |
|---|---|---|---|---|---|
| A. 2',3'-Dideoxy-6-Substituted-Purines of Formula I, Z = H. | | | | | |
| 7a | Cl | CH | 108–110 | 0.35[a] | 82 |
| 8a | OH | CH | 248–250(dec) | 0.24[b] | 45 |
| 9a | $NH_2$ | CH | 198–200 | 0.33[b] | 81 |
| 10a | SH | CH | 263–265(dec) | 0.44[b] | 73 |
| 11a | OH | N | 180–182 | 0.38[b] | 49 |
| 12a | $NH_2$ | N | 220–222(dec) | 0.45[b] | 69 |
| B. 2',3'-Dideoxy-2,6-Disubstituted-Purines of Formula I, Z = $NH_2$. | | | | | |
| 13a | Cl | CH | 145–147 | 0.64 | 80 |
| 14a | OH | CH | 254–256 (dec) | 0.27 | 61 |
| 15a | $NH_2$ | CH | 152–155 | 0.41 | 80 |
| 16a | Cl | N | 153–155 (dec) | 0.69 | 81 |
| 17a | OH | N | 223–225 (dec) | 0.40 | 89 |
| 18a | $NH_2$ | N | 240–242 (dec) | 0.52 | 83 |

[a]$CHCl_3$:MeOH, 10:1.
[b]$CHCl_3$:MeOH, 5:1.

These compounds are candidates for clinical trials in human patients infected with HIV and/or afflicted with AIDS or AIDS-related complex (ARC).

The synthesis of the hydroxymethylcyclopentenyl compounds of formula 7a–18a, from the versatile precursor, 1α-acetylamino-4α-acetoxymethylcyclopent-2-ene (1a) was accomplished as outlined in FIG. 1. Compound 1a was prepared as described in U.S. Pat. No. 4,138,562, the disclosure of which is incorporated by reference herein. Compound 2a was prepared from compound 1a by hydrolysis in the presence of a mild base, such as an alkaline earth metal hydroxide. To afford the pyrimidine compound 3a, Z=H, compound 2a was reacted with an excess of 5-amino-4,6-dichloropyrimidine in the presence of an amine base, such as a trialkylamine, in an alcoholic solvent. Also, 2-amino-4,6-dichloropyrimidine was reacted with compound 2a to yield compound 4a.

Para-chloroaniline was diazotized with acidic sodium nitrite and reacted with compound 4a to yield the chlorophenylazo intermediate 5a. Reduction of the azo intermediate 5a to yield 6a was accomplished with zinc and acetic acid. See Shealy and Clayton, *J. Pharm. Sci.*, 62, 1433 (1973).

The 5-amino-6-chloro-4-pyrimidinyl intermediate 3a was converted to the 9-substituted-6-chloropurine 7a (Z=H) by ring closure with triethylorthoformate and subsequent mild acid hydrolysis to remove ethoxymethylidenes and formates formed during the reaction. In like manner, the 2,5-diamino-6-chloro-4-pyrimidinyl intermediate 6a was ring-closed to the corresponding 2-amino-6-chloro-9H-purin 9-yl compound 13a.

The 6-chloropurines 7a and 13a were converted to the corresponding 6-hydroxy purines 8a and 14a, respectively, with aqueous base, i.e., by refluxing them with an alkali metal hydroxide such as NaOH. Chloro compounds 7a, 13a and 16a were converted to the corresponding amino compounds 9a, 15a and 18a by reaction with liquid ammonia under pressure.

Mono- or di-substituted 6-amino compounds of formula I, wherein X is $NR_2$ and R=R=(lower)alkyl, phenyl or mixtures thereof with H, can be prepared by conventional methods for the conversion of halides to secondary or tertiary amines. For example, see I. T. Harrison et al., *Compendium of Organic Synthetic Methods*, Wiley-Interscience, NY (1971) at pages 250–252. The 6-chloro substituent in compounds 7a, 13a and 16a can be replaced with other halogen atoms by the use of various p-(halo)benzene diazonium chlorides in the conversion of 4a to 5a, or by conventional methods of halide-halide exchange.

These conversions are extensively described in the context of purine nucleoside synthesis in *Nucleoside Analogs-Chemistry, Biology and Medical Applications*, R. T. Walker et al., eds., Plenum Press, NY (1979) at pages 193–223, the disclosure of which is incorporated by reference herein.

Treatment of 7a with thiourea in refluxing alcohol, followed by alkaline hydrolysis afforded thiol 10a. See L. F. Fieser et al., *Reagents for Organic Synthesis*, John Wiley and Sons, Inc., NY (1967) at pages 1165–1167 and U.S. Pat. No. 4,383,114, the disclosures of which are incorporated by reference herein. Phenyl or alkylthio-derivatives can be prepared from the corresponding thiols by the procedure of U.S. Pat. No. 4,383,114 (Example 6).

Ring closure of 3a with acidic aqueous sodium nitrate followed by neutralization with aqueous base directly afforded the corresponding 7-hydroxy-3H-1,2,3-triazolo[4,5d]pyrimidin-3-yl compound 11a. Ring closure of 6a afforded the corresponding 5-amino-7-chloro-3H-1,2,3-triazo[4,5d]pyrimidin-3-yl compound 16a, which was hydrolyzed to the corresponding 7-hydroxy compound 17a with aqueous NaOH. Compound 3a was converted to the corresponding 7-amino compounds 12a by reaction with acidic sodium nitrite, followed by reaction of the crude product with liquid ammonia. Compounds of formula I, wherein Z is OH, X is $NH_2$ or OH, and Y is CH can be prepared from compounds 14a, or by deamination of the 2-amino group with nitrous acid, employing the procedure used by Davoll to convert 2-aminoadenosine to isoguanosine. See J. Davoll, *J. Amer. Chem. Soc.*, 73, 3174 (1951), the disclosure of which is incorporated by reference herein.

Compounds of formula I, wherein X is H, Z is $NH_2$ and Y is CH can be prepared from compounds 7a or 13a by dehalogenation with zinc/water [J. R. Marshall et al., *J. Chem. Soc.*, 1004 (1951)] or by photolysis in dry nitrogen-purged tetrahydrofuran containing 10% triethylamine in a Rayonet photochemical reactor (2537Å) by the method of V. Nair et al., *J. Org. Chem.*, 52, 1344 (1987).

Phosphate or alkanoyl esters of compounds of formula I can be prepared as disclosed in R. Vince (U.S. Pat. No. 4,383,114), the disclosure of which is incorporated by reference herein, employing selective protection of, e.g., the hydroxymethyl or 6-hydroxyl groups, as necessary. Pharmaceutically-acceptable acid salts of compounds 7a–18a can be prepared as described in U.S. Pat. No. 4,383,114, the disclosure of which is incorporated by reference herein.

The invention will be further described by reference to the following detailed examples wherein elemental analyses were performed by M-H-W Laboratories, Phoenix, Ariz. Melting points were determined on a Mel-Temp apparatus and are corrected. Nuclear magnetic resonance spectra were obtained on Jeol FX 90QFT or Nicollet NT300 spectrometers and were recorded in DMSO-$D_6$. Chemical shifts are expressed ppm downfield from $Me_4Si$. IR spectra were determined as KBr pellets with a Nicollet 50XC FT-IR spectrometer, and UV spectra were determined on a Beckmann DU-8 spectrophotometer. Mass spectra were obtained with an AEI Scientific Apparatus Limited MS-30 mass spectrometer. Thin layer chromatography (TLC) was performed on 0.25 mm layers of Merck silica gel 60F-254 and column chromatography on Merck 60 silica gel (230–400 mesh). All chemicals and solvents are reagent grade unless otherwise specified.

Example 1

(±)-(1α, 4α)-4-[(5-Amino-6-chloro-4-pyrimidinyl)-amino]-2 -cyclopentenylcarbinol (3a).

A mixture of 1a (3.0 g, 15 mmol) and aqueous barium hydroxide (0.5N, 300 ml) was refluxed overnight. After cooling, it was neutralized with dry ice. The precipitate was filtered out, and the aqueous solution was concentrated to dryness. The residue was extracted with absolute ethanol and concentrated again to yield 2a, as a colorless syrup 1.6 g (14 mmol).

To this syrup, 5-amino-4,6-dichloropyrimidine (4.59 g, 28 mmol), triethylamine (4.2 g, 42 mmol), and n-butanol (50 ml) were added and the mixture was refluxed for 24 hr. The volatile solvents were removed, the residue was absorbed on silica gel (7 g), packed in a flash column (4.0×12 cm) and eluted with $CHCl_3$-MeOH (20:1) to yield 2.69 g (74%) of compound 3a; mp 130°–132° C. An analytical sample was obtained by recrystalization from ethyl acetate (EtOAc), mp 134°–135° C., MS (30 ev, 200° C.); m/e 240 and 242 ($M^+$ and $M^+$+2), 209 ($M^+$–31), 144 ($B^+$); IR: 3600–2600 (OH), 1620,1580 (C=C, C=N); Anal. ($C_{10}H_{13}ClN_4O$) C,H,N.

Example 2

(±)-(1α,4α)-4-[(2-Amino-6-chloro-4-pyrimidinyl)- amino]-2-cyclopentenylcarbinol (4a).

To 14 mmol of crude 2a, 2-amino-4,6-dichloropyrimidine (3.74 g, 22.8 mmol), triethylamine (15 ml) and n-butanol (75 ml) were added and the mixture was refluxed for 48 hr. The volatile solvents were removed, residue was treated with methanol to separate the undissolved byproduct (the double pyrimidine nucleoside). The methanol solution was absorbed on silica gel (8 g) packed into a column (4.0×14 cm) and eluted with $CHCl_3$-MeOH (40:1) to yield 1.52 g (42%) of crude 4a. The product was recrystalized from ethyl acetate to yield 4a; mp 132°–134° C., MS (30 ev, 200° C.); m/e 240 and 242 ($M^+$ and $M^+$+2), 209 ($M^+$–31), 144 ($B^+$); IR: 3600–3000 ($NH_2$, OH), 1620,1580 (C=C, C=N); Anal. ($C_{10}H_{13}ClN_4O$) C,H,N.

Example 3

(±)-(1α,4α)-4-{[2-Amino-6-chloro-5-(4-chlorophenyl)-azo]-4-pyrimidinyl]-amino}-2-cyclopentenylcarbinol (5a).

A cold diazonium salt solution was prepared from p-chloroaniline (1.47 g, 11.5 mmol) in 3N HCl (25 ml) and sodium nitrite (870 mg, 12.5 mmol) in water (10 ml). This solution was added to a mixture of 4a (2.40 g, 10 mmol), acetic acid (50 ml), water (50 ml) and sodium acetate trihydrate (20 g). The reaction mixture was stirred overnight at room temperature. The yellow precipitate was filtered and washed with cold water until neutral, then it was air-dried in the fumehood to yield 3.60 g (94%), of 5a, mp 229° C. (dec). The analytical sample was obtained from acetone-methanol (1:2), mp 241°–243° C. (dec). MS (30 ev, 260° C.): m/e 378 and 380 ($M^+$ and $M^+$+2), 282 ($B^+$); IR: 3600–3000 ($NH_2$, OH), 1620,1580 (C=C, C=N); Anal. ($C_{16}H_{16}Cl_2N_6O$) C,H,N.

Example 4

(±)-(1α,4α)-4-[(2,5-Diamino-6-chloro-4-pyrimidinylamino]-2 cyclopentenylcarbinol (6a).

A mixture of 5a (379 mg, 1 mmol), zinc dust (0.65 g, 10 mmol), acetic acid (0.32 ml), water (15 ml) and ethanol (15 ml) was refluxed under nitrogen for 3 hr. The zinc was removed and the solvents were evaporated. The residue was absorbed on silica gel (2 g), packed into a column (2.0×18 cm), and eluted with $CHCl_3$-MeOH (15:1). A pink syrup was obtained. Further purification from methanol-ether yielded 6a as pink crystals, 170 mg (66%), mp 168°–170° C., MS (30 ev, 220° C.); m/e 255 and 257 ($M^+$ and $M^+$+2), 224 ($M^+$–31), 159 ($B^+$); IR: 3600–3000 ($NH_2$, OH), 1620,1580 (C=C, C=N); Anal. ($C_{10}H_{14}ClN_5O$) C,H,N.

Example 5

(±)-(1α,4α)-4-(6-chloro-9H-purin-9-yl)-2 -cyclopentenylcarbinol (7a).

A mixture of 3a (1.30 g, 5.4 mmol), triethyl orthoformate (30 ml) and hydrochloric acid (12 N, 0.50 ml) was stirred overnight at room temperature. The solvent was evaporated at 35° C. in vacuo. To the residue was added aqueous hydrochloric acid (0.5 N, 30 ml) and the mixture was stirred for 1 hr. The mixture was neutralized to pH 7–8 with 1 N sodium hydroxide and absorbed onto silica gel (8 g), packed in a column (4.0×8 cm), and eluted with $CHCl_3$-MeOH (20:1) to yield white crystals of 7a, 1.12 g (82%). The crude product was recrystalized from ethyl acetate to yield 7a, mp 108°–110° C., MS (30 ev, 200° C.); m/e 250 and 252 ($M^+$ and $M^+$+2), 219 ($M^+$–31), 154 ($B^+$); IR: 3600–2800 (OH), 1600 (C=C, C=N); Anal. ($C_{11}H_{11}ClN_4O$) C,H,N.

Example 6

(±)-(1α,4')-4-(6-Hydroxy-9H-purin-9-yl)-2 -cyclopentenylcarbinol (8a).

A mixture of 7a (251 mg, 1 mmol) and aqueous sodium hydroxide (0.2 N, 10 ml) was refluxed for 3 hr. After cooling, the reaction mixture was adjusted to pH 5–6 with acetic acid. The reaction mixture was absorbed on silica gel (2 g) packed in a column (2.0×11 cm) and eluted with $CHCl_3$-MeOH (10:1) to yield 105 mg (45%) of 8a. The crude white product was recrystalized from water-methanol (3:1) to yield 8a., mp 248°–250° C. (dec), MS (30 ev, 300° C.); m/e 232 ($M^+$), 214 ($M^+$–18), 136 ($B^+$); IR; 3600–2600 (OH), 1680,1600 (C=O, C=C, C=N); Anal. ($C_{11}H_{12}N_4O_2$) C,H,N.

Example 7

(±)-(1α,4α)-4-(6-Amino-9H-purin-9-yl)-2 -cyclopentenylcarbinol (9a).

Liquid ammonia was passed into a bomb containing a solution of 7a (250 mg, 1 mmol) in methanol (5 ml) at −80° C. The bomb was sealed and heated at 60° C. for 24 hr. Ammonia and methanol were evaporated and the residue was recrystalized from water to yield off-white crystals of 9a, 187 mg (81%),.mp 198°–200° C., MS (30 ev, 210° C.): m/e 231 ($M^+$), 213 ($M^+$–18), 135 ($B^+$); IR: 3600–2600 ($NH_2$, OH), 1700,1600 (C=C, C=N); Anal. ($C_{11}H_{13}N_5O$) C,H,N.

Example 8

(±)-(1α,4')-4-(6-Mercapto-9H-purin-9-yl)-2-cyclopentenylcarbinol (10a).

A mixture of 7a (125 mg, 0.5 mmol), thiourea (40 mg, 0.64 mmol) and n-propanol (5 ml) was refluxed for 2 hr. After cooling, the precipitate was isolated by filtration, washed with n-propanol, and dissolved in sodium hydroxide (1N, 5 ml). The solution was adjusted to pH 5 with acetic acid. The crude 10a (90 mg, 73%) was isolated again, mp 260°–262° C. (dec) and was recrystalized from N,N-dimethylformamide, to yield 10a, mp 263°–265° C. (dec). MS (30 ev, 290° C.): m/e 248 (M$^+$), 230 (M$^+$–18), 152 (B$^+$); IR: 3600–3200 (OH), 3100,2400 (SH), 1600 (C=C, C=N); Anal. ($C_{11}H_{12}N_4OS$) C,H,N.

Example 9

(±)-(1α,4α)-4-(7-Hydroxy-3H-1,2,3-triazolo[4,5-d]pyrimidin-3-yl)-2-cyclopentenyl carbinol (11a).

To a cold solution of 3a (361 mg, 1.5 mmol) in hydrochloric acid (1 N, 30 ml) was added sodium nitrite solution (120 mg, 1.7 mmol) in 3 ml of water. The reaction was monitored by starch-potassium iodide paper. The mixture concentrated at 40° C. to a volume of 2 ml and adjusted to pH 7 with aqueous sodium hydroxide. The mixture was absorbed on silica gel (2 g), packed in a column (2.0×13 cm) and eluted with CHCl$_3$-MeOH (10:1). The crude 11a was recrystallized from water-methanol (3:1) to yield white crystals of 11a, 173 mg (49%) mp 180°–182° C. MS (30 ev, 230° C.): m/e 233 (M$^+$), 203 (M$^+$–30), 137 (B$^+$); IR: 3600–2600 (OH), 1740,1600 (C=O, C=C, C=N); Anal. ($C_{10}H_{11}N_5O_2$) C,H,N.

Example 10

(±)-1α,4α)-4-(7-Amino-3H-1,2,3-triazolo[4,15d]pyrimidin-3-yl)-2-cyclopentenyl carbinol (12a).

Sodium nitrite solution (828 mg, 12 mmol) in water (10 ml) was added dropwise to a cold solution of 3a (2.43 g, 10.1 mmol) in hydrochloric acid (0.5 N, 40 ml). The reaction mixture was stirred at room temperature for 1 hr, then concentrated to a syrup. The syrup was dissolved in ethanol and transferred into a stainless steel bomb. Liquid ammonia was passed in, the bomb was sealed, and the reaction mixture was stirred at room temperature overnight. Ammonia was evaporated and the residue was chromatographed on silica gel (150 g) eluting with CH$_2$Cl$_2$-MeOH (10:1) to yield white crystals of 12a, 1.62 g (69%), mp 220°–222° C. (dec). MS (30 ev, 220° C.): m/e 232 (M$^+$), 202 (M$^+$–30), 136 (B$^+$); IR: 3600–2800 (NH$_2$, OH), 1700,1600 (C=C, C=N); Anal. ($C_{10}H_{12}N_6O$) C,H,N.

Example 11

(±)-(1α,4α)-4-(2-Amino-6-chloro-9H-purin-9-yl)-2-cyclopentenyl carbinol (13a).

A mixture of 6a (1.41 g, 5.5 mmol) triethyl orthoformate (30 ml) and hydrochloric acid (12 N, 1.40 ml) was stirred overnight. The suspension was dried in vacuo. Diluted hydrochloric acid (0.5 N, 40 ml) was added and the mixture was reacted at room temperature for 1 hr. The mixture was neutralized to pH 8 with 1 N sodium hydroxide and absorbed on silica gel (7.5 g) packed in a column (4.0×10 cm) and eluted by CHCl$_3$-MeOH (20:1) to yield off-white crystals of 13a, 1.18 g (80%). The crude product was recrystalized from ethanol to yield 13a, mp 145°–147° C. MS (30 ev, 220° C.): m/e 265 and 267 (M$^+$ and M++2), 235 (M$^+$–30), 169 (B$^+$); IR: 3600–2600 (NH$_2$, OH), 1620,1580 (C=C, C=N); Anal. ($C_{11}H_{12}N_5OCl^a$3/4 H$_2$O) C, H, N.

Example 12

(±)-(1α,4α)-4-(2-Amino-6-hydroxy-9H-purin-9-yl)-2-cyclopentenyl carbinol (14a).

A mixture of 13a (266 mg, 1 mmol) and aqueous sodium hydroxide (0.33 N) was refluxed for 5 hr., absorbed onto silica gel (2 g) packed in a column (2.0×7.5 cm) and eluted with CHCl$_3$-MeOH (5:1). The crude product was recrystalized from methanol-water (1:4) to yield white crystals of 14a, 152 mg (61%), mp 254°–256° C. (dec). MS (30 ev, 200° C.): m/e 247 (M$^+$), 217 (M$^+$–30), 151 (B$^+$); IR: 3600–2600 (NH$_2$, OH), 1700,1600 (C=O, C=C, C=N); Anal. ($C_{11}H_{13}N_5O_2{}^a$3/4 H$_2$O) C,H,N.

Example 13

(±)-(1α,4α)-4-(2,6-Diamino-9H-purin-9-yl)-2-cyclopentenyl-carbinol (15a).

Liquid ammonia was passed into a solution of 13a (265 mg, 1 mmol) in methanol (10 ml) at –80° C in a bomb. The bomb was sealed and heated at 75° C. for 48 hr. Ammonia and methanol were evaporated. The residue was absorbed on silica gel (2 g), packed in a column (2.0×10 cm) and eluted with CHCl$_3$-MeOH (15:1). The crude product was recrystalized from ethanol to yield 196 mg (80%) of 15a, mp 152°–155° C. MS (30 ev, 200° C.): m/e 246 (M$^+$), 229 (M$^+$–17), 216 (M$^+$–30), 150 (B$^+$); IR: 3600–3000 (NH$_2$, OH), 1700,1650, –1600 (C=O, C=C, C=N); Anal. ($C_{11}H_{14}N_6O$) C,H,N.

Example 14

(±)-(1α,4α)-4-(5-Amino-7-chloro-3H-1,2,3-triazolo[4,5d]-pyrimidin-3-yl)-2-cyclopentenyl carbinol (16a).

To a cold solution of 6a (225 mg, 1 mmol) in acetic acid (1.5 ml) and water (2.5 ml) was added sodium nitrite (83 mg, 1.2 mmol) in water (2 ml). The reaction was monitored by starch-potassium iodide paper. After stirring for 1 hr. at 0° C., the precipitate was filtered and washed with cold water, then dried over phosphorus pentoxide in vacuo to yield 16a as off-white crystals, 218 mg (81%). The crude 16a was recrystalized from methanol, mp 153+–155° C. (dec). MS (30 ev, 220° C.): m/e 266 and 268 (M$^+$ and M$^+$+2), 236 (M$^+$–30), 170 (B$^+$); IR: 3600–3000 (NH$_2$, OH), 1650,1600 (C=C, C=N); Anal. ($C_{10}H_{11}ClN_6O$) C,H,N.

Example 15

(±)-(1α,4α)-4-(5-Amino-7-hydroxy-3H-1,2,3-triazolo[4,5-d]-pyrimidin-3-yl)-2-cyclopentenyl carbinol (17a).

A mixture of 16a (218 mg, 0.8 mmol) and aqueous sodium hydroxide (0.25 N, 10 ml) was refluxed for 3 hr, then was adjusted to pH 3 with 6 N hydrochloric acid. The gelatinious precipitate was filtered and washed with cold water. It was dried over phosphorous pentoxide in vacuo to yield 17a as an off-white solid, 181 mg (90%) mp 222°–224° C. (dec).

After recrystalization from water, the mp was 223°–225° C. (dec). MS (20 ev, 300° C.): m/e 248 (M$^+$), 217 (M$^+$–31), 152 (B$^+$); IR: 3600–3000 (NH$_2$, OH), 1750,1600 (C=C, C=N); Anal. (C$_{10}$H$_{12}$N$_6$O$_1$.1/2 H$_2$O) C,H,N.

Example 16

(±)-(1α,4α)-4-(5,7-Diamino-3H-1,2,3-triazolo[4,5-d]pyrimidin-3-yl)-2-cyclopentenyl carbinol (18a).

Compound 16a (267 mg, 1 mmol) was processed as described in Example 13, employing a reaction time of 60° C. for 20 hr. The residual mixture was absorbed on silica gel (2 g), packed in a column (2.0×10 cm) and eluted by CHCl$_3$-MeOH (15:1) to yield 18a as white crystals, 204 mg (83%). The crude product was recrystalized from ethanol-water (2:1), to yield 18a of mp 240°–242° C. (dec). MS (30 ev, 240° C.): m/e 247 (M$^+$), 229 (M$^+$–18), 217 (M$^+$–30), 151 (B$^+$); IR: 3600–3100 (NH$_2$, OH), 1700,1650,1600 (C=O, C=C, C=N); Anal. (C$_{10}$H$_{13}$N$_7$O. H$_2$O) C,H,N.

Example 17

(±)-(1α,4α)-4-(3-Methoxy-2-methylacryloylureido)-2-cyclopentenyl carbinol (19a).

Isocyanate reagent was prepared from 3-methoxy-2-methylacryloyl chloride (1.00 g, bp 65°–66° C./2.5 mm) in anhydrous benzene (10 ml) and freshly dried silver cyanate (2.6 g, 17 mmol, dried at 110° C., 2 hrs) by refluxing for 0.5 hr. The supernatant was added dropwise into a solution of 2a (from 1a, 0.8 g, 4 mmol) in N,N-dimethylformamide (10 ml) at −15° C. and the mixture was stirred for 1 hr, then stored at 4° C. overnight. The solvent was evaporated and the residue was absorbed on silica gel (3 g), packed in a column (2.0×16 cm) and eluted with CHCl$_3$-MeOH (20:1) to yield white crystals of 19a, 605 rag, (60%), mp 147°–149° C. MS (30 ev, 200° C.): m/e 254 (M$^+$), 239 (M$^+$–15), 223 (M$^+$–31), 158 (B$^+$); IR: 3600–2800 (NH$_2$, OH), 1700,1650,1600 (C=O, C=C); Anal. (C$_{12}$H$_{18}$N$_2$O$_4$) C,H,N.

Example 18

(±)-(1α,4α)-4-[5-Methyl-2,4-(1H,3H)-pyrimidinedion-3-yl]-2-cyclopentenl carbinol (20a).

A mixture of 19a (381 mg, 1.5 mmol), p-toluene-sulfonic acid monohydrate (20 mg) and anhydrous N,N-dimethylformamide (2 ml) was stirred at 115° C. for 3 hr. The solvent was evaporated, the residue was absorbed on silica gel (3 g), packed in a column (2.0×14 cm) and eluted with CHCl$_3$-MeOH (20:1) to yield 20a as off-white crystals, 206 mg (62%). The product was recrystalized from absolute ethanol to yield 20a, mp 213°–215° C. MS (30 ev, 250° C.): m/e 222 (M$^+$), 204 (M$^+$–18), 191 (M$^+$–31), 126 (B$^+$); IR: 3600–3300 (OH), 1700,1600 (C=O, C=C); Anal. (C$_{11}$H$_{14}$N$_2$O$_3$) C,H,N.

Example 19

Esterification of Compound 14a.

(1α,4α)-4-(2-Amino-6-hydroxy-9H-purin-9-yl)-2-cyclopentenyl Acetoxycarbinol.

To a suspension of 14a (130 mg, 0.50 mmol) and 4-dimethylaminopyridine (5 mg, 0.04 mmol) in a mixture of acetonitrile (6 ml) and triethylamine (0.09 ml, 0.66 mmol) was added acetic anhydride (0.06 ml, 0.6 mmole). The mixture was stirred at room temperature for 3 hr. Methanol (1 ml) was added to quench the reaction. The solution was concentrated and absorbed on silica gel (1.5 g), packed on a column (2.0×12 cm), and eluted with CHCl$_3$-MeOH (20:1). The product fractions were collected and concentrated to yield a white solid. The solid product was washed with MeOH-AcOEt to yield 123 mg of the purified acetoxy-carbinol (85%). Further purification from methanol afforded needle-like crystals, mp 237°–239° C.; Anal. (C$_{13}$H$_{15}$N$_5$O$_3$) C,H,N.

Example 20

(1S,4R)-4-(2-Amino-6-hydroxy-9H-Purin-9-yl)-2-cyclopentenyl Carbinol ((−)14a).

The diamino analog, 15a, (100 mg) was dissolved in 3 ml of 0.05 M K$_2$PO$_4$ buffer (pH 7.4) at 50° C. The solution was cooled at 25° C. and 40 units of adenosine deaminase (Sigma, Type VI, calf intestinal mucosa) was added. After three days of incubation at room temperature, a precipitate formed and was removed by filtration to yield 18.2 mg of crude product. The filtrate was concentrated to 1.5 ml and refrigerated for 2 days. Additional solid (26.8 mg) was obtained by filtration. The two solid fractions were recrystalized from water to yield the pure product, mp 269°–272° C.; [α]$_D^{24}$ −62.1 (c 0.3 MeOH).

Example 21

(1R,4S)-4-(2-Amino-6-hydroxy-9H-purin-9-yl)-2-cyclopentenyl carbinol ((+)14a).

The filtrates from the preparation of the 1S,4R isomer were combined and evaporated to dryness. The unchanged diamino starting material was separated on a silica gel flash column using 10% methanol/chloroform. The diamino compound was dissolved in 0.05M K$_2$PO$_4$ buffer, pH 7.4 (15 ml) and 800 units of adenosine deaminase was added. The solution was incubated for 96 hr at 37° C. TLC indicated some unreacted product remained. The solution was heated in boiling water for 3 min and filtered to remove denatured protein. Another 800 units of adenosine deaminase was added and the processes were repeated. The deproteinated solution was evaporated to dryness and the product was crystalized from water to yield a white solid; mp 265°–270° C.; [α]$_D^{24}$ +61.1 (c 0.3 MeOH).

Example 22

Cytotoxicity Assay.

The ED$_{50}$ cytotoxicity concentrations determined for analogs 7a, 9a, 10a, 16a, and 17a in the P-388 mouse leukemia cell culture assay are given in Table II.

TABLE II

Inhibitory Concentrations of
Carbocyclic Nucleosides for P-388
Leukemia Cells in Cultures*

| Compound | $ED_{50}$, µg/ml |
|---|---|
| 7a | 12.0 |
| 9a | 40.0 |
| 10a | 3.0 |
| 16a | 1.0 |
| 17a | 4.5 |

*Assay Technique: R. G. Almquist and R. Vince, J. Med. Chem., 16, 1396 (1973).

Therefore, all of the compounds listed on Table II are active against P-388 mouse leukemia.

Example 23

Anti-HIV Assay

Compounds of formula I were screened for anti-HIV activity at the National Cancer Institute, Frederick Cancer Research Facility, Frederick, Md. (FCRF). The following are the current screening mode operational procedures utilized at FCRF. The protocol consists of 3 areas, (I) preparation of infected cells and distribution to the test plates, (II) preparation of drug dilution plates and distribution to the test plates, and (III) XTT assay procedure. See D. A. Scudiero et al., "A New Simplified Tetrazolium Assay for Cell Growth and Drug Sensitivity in Culture," Cancer Res., 48, 4827 (1988).

I. Infection and Distribution of Cells to Microtiter Trays

Cells to be infected (a normal lymphoblastoid cell line which expresses CD4) are placed in 50 ml conical centrifuge tubes and treated for 1 hr with 1–2 µg/ml of polybrene at 37° C. The cells are then pelleted for 8 min. at 1200 rpm. HIV virus, diluted 1:10 in media (RMP1-1640, 10% human serum or 15% fetal calf serum (FCS), with IL-2, for ATH8 cells only, and antibiotics) is added to provided and MOI of 0.001. Medium alone is added to virus-free control cells Assuming an infectious virus titer of $10^{-4}$, and MOI of 0.001 represents 8 infectious virus particles per 10,000 cells. About 500,000 cells/tube are exposed to 400 µl of the virus dilution. The resultant mixture is incubated for 1 hr at 37° C. in Air-$CO_2$. The infected or uninfected cells are diluted to give $1 \times 10^{-4}$ (with human serum or $2 \times 10^{-4}$ with fetal calf serum) cells/100 µl.

Infected or uninfected cells (100 µl) are distributed to appropriate wells of a 96 well, U-bottom, microtiter plate. Each compound dilution is tested in duplicate with infected cells. Uninfected cells are examined for drug sensitivity in a single well for each dilution of compound. Drug-free control cells, infected and uninfected, are run in triplicate. Wells B2 through G2 served as reagent controls and received medium only. The plates are incubated at 37° C. in Air-$CO_2$ until the drug is added.

II. Drug Dilution and Addition

Dilution plates (flat bottom 96 well, microtiter plates) are treated overnight with phosphate buffered saline (PBS) or media containing at least 1% FCS or 1% human serum (depending on the medium used in the test), beginning the day before assay. This "blocking" procedure is used to limit the adsorption of drug to the microtiter tray during the dilution process. The wells are filled completely with the blocking solution and allowed to stand at room temperature in a humidified chamber in a hood.

The dilution process is begun by first diluting the test compound 1:20. Blocked, dilution plates are prepared by flicking out the blocking solution and blotting dry on sterile gauze. All wells of each plate are then filled with 225 µl of the appropriate medium using a Cetus liquid handling system. Twenty-five microliters (25 µl) of each 1:20 diluted compound is then manually added to row A of a blocked and filled dilution plate. Four compounds, sufficient to supply two test plates, are added per dilution plate. The four compounds are then serially diluted ten-fold from row A through row H using the Cetus liquid handling system. The starting dilution of each compound in row A is, at this point, 1:200. The dilution plates are kept on ice until needed.

Using a multi-channel pipettor with 6 microtips, 100 µl of each drug dilution is transferred to the test plate which already contains 100 µl of medium plus cells. The final dilution, in the test plate, starts at 1:400 (wells B4 through G4). This dilution (to 0.25% DMSO) prevents the DMSO vehicle from interfering with cell growth. Drug-free, infected or uninfected cells (wells B3 through G3) and reagent controls (B2 through G2) receive medium alone. The final two compounds are then transferred from wells H7 through H12 to a second test plate using the same procedure. Test plates are incubated at 37° C. in Air-$CO_2$ for 7–14 days or until virus controls are lysed as determined macroscopically.

III. Quantitation of Viral Cytopathogenicity and Drug Activity

A. Materials

1. A solution of 2,3-bis[2-methoxy-4-nitro-5 -sulfophenyl]-5-[(phenylamino) carbonyl]-2H-tetra-zolium hydroxide. (XTT)—1 mg/ml solution in media without FCS. Store at 4° C. Prepare weekly.

Phenazine methosulfonate (PMS) stock solution—This can be prepared and maintained frozen until needed at −20° C. It should be made in PBS to a concentration of 15.3 mg/ml.

B. Microculture Tetrazolium Assay (MTA)

1. Preparation of XTT-PMS Solution—The XTT-PMS is prepared immediately prior to its addition to the wells of the culture dish. The stock PMS solution is diluted 1:100 (0.153 mg/ml). Diluted PMS is added to every ml of XTT required to give a final PMS concentration of 0.02 mM. A 50 µl aliquot of the XTT-PMS mixture is added to each of the appropriate wells, and the plate is incubated for four hours at 37° C. The plate lids are removed and replaced with adhesive plate sealers (Dynatech cat 001-010-3501). The sealed plate is shaken on a microculture plate mixer and the absorbance is determined at 450 nm.

IV. Results

Figure 2:
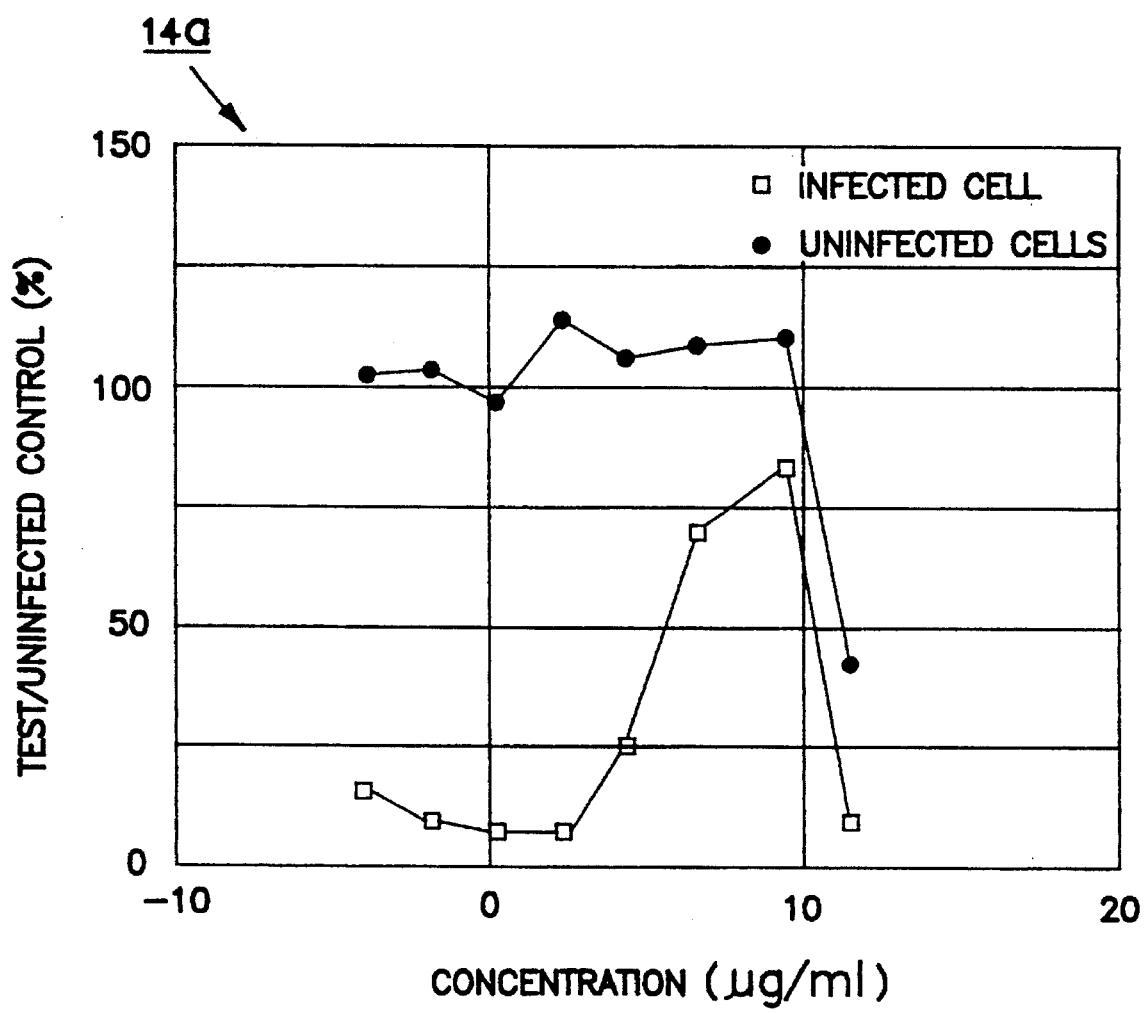
FIG. 2 is a graphic depiction of cells exposed to 14a/ control cells (%) plotted vs. concentration of 14a for both uninfected cells and cells infected with HIV.

FIG. 2 depicts a plot of the percentage of test cells over uninfected cells (%) for both infected and uninfected cells as a function of the increasing concentration of compound 14a.

The data plotted on FIG. 2 permit the calculation of an effective concentration ($EC_{50}$) with respect to infected cells of about 0.15 µg/ml, an inhibitory concentration ($IC_{50}$) with respect to normal cells of about 100 µg/ml, and a therapeutic index ($TI_{50}$) of about 667. An earlier assay carried out at the Southern Research Institute yielded a $TI_{50}$ of about 200 when MT-2 cells were cultured with H9/HTLV-IIIB.

The HIV inhibitory concentrations of compounds 7a, 9a, 10a, 13a, 14a, and 15a are given on Table III, below.

TABLE III

| HIV Inhibitory Concentrations[a] | |
|---|---|
| Compound | $ED_{50}$ (μg/ml) |
| 7a | >10 |
| 9a | 2.3 |
| 10a | >10 |
| 13a | 0.41 |
| 14a | 0.15 |
| 15a | 2.9 |
| (–)14a | 0.66 |

[a]MT-2 host cells, except (–)14a, which was assayed in CEM cells, exhibiting an $IC_{50}$ of 189.

Compound 14a was also found to be active against feline leukemia virus ($ED_{50}$=9; FAIDS variant); murine leukemia virus ($ED_{50}$=1.1; Cas-BR-M type) and simian AIDS virus ($ED_{50}$=2.8; D/Washington type).

The invention comprises the biologically active compounds as disclosed or the pharmaceutically acceptable salts or esters thereof, together with a pharmaceutically acceptable carrier for administration in effective nontoxic dose form. Pharmaceutically acceptable salts may be salts of organic acids, such as acetic, lactic, malic or p-toluene sulphonic acid and the like as well as salts of pharmaceutically-acceptable mineral acids, such as hydrochloric or sulfuric acid and the like. Other salts may be prepared and then converted by conventional double decomposition methods into pharmaceutically-acceptable salts directly suitable for purposes of treatment of viral infections in mammals or for the prevention of viral contamination of physiological fluids such as blood or semen in vitro.

Pharmaceutically acceptable carriers are materials useful for the purpose of administering the present analogs and may be solid, liquid or gaseous materials, which are otherwise inert and medically acceptable and are compatible with the active ingredients. Thus, the present active compounds can be combined with the carrier and added to physiological fluids in vitro or administered in vivo parenterally, orally, used as a suppository or pessary, applied topically as an ointment, cream, aerosol, powder, or given as eye or nose drops, etc., depending upon whether the preparation is used for treatment of internal or external viral infections.

For internal viral infections, the compositions may be administered orally or parenterally at effective non-toxic antivirus dose levels of about 10 to 750 mg/kg/day of body weight given in one dose or several smaller doses throughout the day. For oral administration, fine powders or granules may contain diluting, dispersing and/or surface active agents and may be presented in water or in a syrup; in capsules in the dry state, or in a non-aqueous solution or suspension; in tablets or the like. Where desirable or necessary, flavoring, preserving, suspending, thickening, or emulsifying agents may be included. For parenteral administration, administration as drops, the compounds may be presented in aqueous solution in an effective, non-toxic dose in concentration of from about 0.1 to 10 percent w/v. The solutions may contain antioxidants, buffers and the like. Alternatively, for infections of external tissues, the compositions are preferably applied as a topical ointment or cream in concentration of about 0.1 to 10 percent w/v.

Projected Clinical Trial to Evaluate Ability of Compound 14a+AZT to Inhibit the Progression of HIV Infection AZT administration can decrease mortality and the frequency of opportunistic infection in subjects with AIDS or AIDS-related complex. M. A. Fischl et al. *New Engl. J. Med.*, 317, 185 (1987). Therefore, many persons who have been diagnosed HIV-positive are presently receiving daily doses of AZT. However, AZT is myelotoxic and its administration over a period of 2–3 years has recently been shown to either cause, or to fail to inhibit, a high incidence of the development of non-Hodgkins lymphoma. Therefore, the present study is designed to evaluate the ability of compound (–)14a to inhibit the course of HIV infection.

Patients and Methods

Sixty patients, thirty with HIV infection plus AIDS-related complex and thirty with early AIDS are selected and evaluated in accord with the criteria provided by M. A. Fischl et al., cited above. The two groups of thirty patients are matched into pairs. A capsule containing 100 mg of AZT or an indistinguishable capsule containing 50 mg AZT and 50 mg of (–)14a is administered orally every 4 hours throughout the 24-hour day, for 24 weeks. All of the ARC patients complete the entire study and 20 of the AIDS patients complete the study.

Results

Development of AIDS in ARC Patients

Four patients in the AZT group but none in the AZT+14(a) group develop opportunistic infections or Kaposi sarcoma. Of the four patients in whom AIDS develops: 1 has PCP, candida pneumonia and cerebral toxoplasmosis; 2 have PCP alone and 1 has non-Hodgkins lymphoma in the breast and Kaposi sarcoma in a lymph node. Three of the four patients die 8, 15 and 18 months after diagnosis.

Clinical Progression of AIDS

Nine of the AIDS patients treated with AZT alone die during the study while there is only one death in the population treated with (–)14a plus AZT. During the treatment period, two of fifteen patients who receive the combination regimen worsen while, of the survivors, five of six patients receiving AZT alone worsen. The criteria for response are those of M. A. Fischl et al., cited above.

Discussion

Oral (–)14a+AZT administered in a 1:1 weight ratio is superior to an equivalent amount of AZT in reducing mortality due to early AIDS and the progression of HIV infection in both ARC and early AIDS patients, for a period of up to 6 months. This study also validates the in vitro model used herein to establish the anti-HIV activity of members of this class of carbocyclic nucleosides.

The invention has been described with reference to various specific and preferred embodiments and techniques. However, it should be understood that many variations and modifications may be made while remaining within the spirit and scope of the invention.

What is claimed is:

1. A therapeutic method comprising administering to a human infected with HIV, an amount of a compound of the formula:

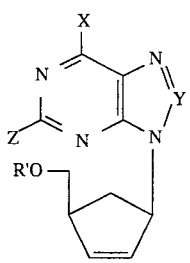

wherein Z is NH$_2$, R' is H, (C$_1$–C$_{16}$)alkanoyl or O=P(OH)$_2$; Y is CH, and X is selected from the group consisting of OR, H, or N(R)$_2$, wherein each R is H or (C$_1$–C$_4$)alkyl, and the pharmaceutically acceptable salts thereof, wherein said amount is effective to inhibit the course of HIV infection.

2. The method of claim 1 wherein R' is H and X is OH.

3. The method of claim 2 wherein the compound is (1'R, 4'S)-2-amino-1,9-dihydro-9 -[4'-hydroxymethyl-2'-cyclopenten-1-yl]-6H-purin-6-one.

4. The method of claim 1 wherein R' is H and X is H.

5. The method of claim 1 wherein R' is H and X is NH$_2$.

6. The method of claims 1, 2 or 3 wherein the compound is combined with a pharmaceutically acceptable carrier.

7. The method of claim 6 wherein the compound is administered to a human infected with HIV.

8. The method of claim 6 wherein the compound is administered to a human infected with HIV at about 10–750 mg/kg/day of body weight.

9. The method of claim 6 wherein the compound is administered to a human afflicted with AIDS.

10. The method of claim 6 wherein the compound is administered to a patient afflicted with AIDS-related complex.

11. The method of claim 6 wherein the compound is administered in a single dose.

12. The method of claim 6 wherein the compound is administered in multiple doses.

13. The method of claim 6 wherein the compound is administered parenterally.

14. The method of claim 13 wherein the compound is administered in the form of a suppository, a pessary, a topical application, or drops.

15. The method of claim 13 wherein the topical application is in the form of an ointment, a cream, an aerosol, or a powder.

16. The method of claim 13 wherein the drops are an aqueous solution.

17. The method of claim 16 wherein the drops comprise 0.1–10% w/v of the compound.

18. The method of claim 6 wherein the compound is administered orally.

19. The method of claim 18 wherein the compound is administered in the form of a liquid, a powder, granules, a capsule, or a tablet.

20. The method of claim 19 wherein the powder or granules contain a diluting agent, a dispersing agent, a surface active agent, or a combination thereof.

21. The method of claim 19 wherein the capsule contains the composition in a dry state, a non-aqueous solution, or a non-aqueous suspension.

22. The method of claim 1 wherein N(R)$_2$ is NH[(C$_1$–C$_4$)alkyl].

* * * * *

UNITED STATES PATENT AND TRADEMARK OFFICE
CERTIFICATE OF CORRECTION

PATENT NO. : 5,567,703
DATED : October 22, 1996
INVENTOR(S) : Robert Vince et al.

It is certified that error appears in the above-indentified patent and that said Letters Patent is hereby corrected as shown below:

At Column 6, line 35, please delete "14a, or by" and insert --14a or 15a by--.

At Claim 6, Column 17, line 23, please delete "claims" and insert --claim--.

Signed and Sealed this

Thirtieth Day of September, 1997

Attest:

BRUCE LEHMAN

Attesting Officer

Commissioner of Patents and Trademarks